United States Patent [19]

Karami

[11] Patent Number: 4,527,989
[45] Date of Patent: Jul. 9, 1985

[54] ELASTICIZED DISPOSABLE DIAPER

[75] Inventor: Hamzeh Karami, Embourg, Belgium

[73] Assignee: Colgate-Palmolive Company, New York, N.Y.

[21] Appl. No.: 458,515

[22] Filed: Jan. 17, 1983

Related U.S. Application Data

[63] Continuation-in-part of Ser. No. 314,907, Oct. 26, 1981, abandoned, which is a continuation of Ser. No. 99,784, Dec. 3, 1979, abandoned.

[51] Int. Cl.³ .............................................. A61F 13/16
[52] U.S. Cl. ................................................ 604/385 A
[58] Field of Search ................ 604/385, 385 R, 385 A

[56] References Cited

U.S. PATENT DOCUMENTS

| | | | |
|---|---|---|---|
| 4,050,462 | 9/1977 | Woon et al. | 604/385 |
| 4,069,822 | 1/1978 | Buell | 604/366 |
| 4,253,461 | 3/1981 | Strickland et al. | 604/389 |
| 4,259,958 | 4/1981 | Goodbar | 604/374 |
| 4,324,245 | 4/1982 | Mesek et al. | 604/385 |
| 4,325,372 | 4/1982 | Teed | 604/385 |

Primary Examiner—C. Fred Rosenbaum
Assistant Examiner—Sherri E. Vinyard
Attorney, Agent, or Firm—Herbert S. Sylvester; Murray M. Grill; Norman Blumenkopf

[57] ABSTRACT

A disposable diaper having elasticized crotch seals formed from elastic members secured to the backing sheet within ¾ inch of the absorbent pad and entirely overlying the ears of the contoured pad to assure such tension as to minimize transverse pleats in the crotch area.

1 Claim, 3 Drawing Figures 4,527,989

ELASTICIZED DISPOSABLE DIAPER

REFERENCE TO RELATED APPLICATIONS

This application is a continuation-in-part of application Ser. No. 314,907, filed Oct. 26, 1981, now abandoned which in turn was a continuation of application Ser. No. 99,784, filed Dec. 3, 1979 now abandoned.

BACKGROUND OF THE INVENTION

1. Field of the Invention

This invention relates to disposable diapers and more particularly to an elasticized and contoured diaper.

2. Description of the Prior Art

In the past elasticized contoured diapers have been developed such as that disclosed in the patents to Buell, U.S. Pat. No. 3,860,003, issued Jan. 14, 1975 for "Contractable Side Portions for Disposable Diaper," and U.S. Pat. No. 4,069,822, issued Jan. 24, 1978 for "Porous Fibrous Web Bonded to a Substrate and Articles Therefrom," wherein elastic strips are secured to the crotch portions of the diaper and spaced at least $\frac{3}{4}$ inch from the absorbent pad to form elasticized crotch seals for securement over the legs of the infant to prevent loss of fluid from the interior of the diaper along the legs of the infant. The elasticized strips were placed more than $\frac{3}{4}$ inch from the absorbent pad in order to prevent pleats forming transversely of the crotch area of the diaper. Further, in U.S. Pat. No. 4,069,822, the elasticized members do not extend entirely over the ears of the absorbent pad.

Another diaper is presently in production in which the elasticized strips are less than $\frac{3}{4}$ inch from the absorbent pad for the production of the transverse pleats in the crotch area of the diaper for the purpose of increasing the absorbent capacity at the crotch area of the diaper. However, it has been found that these pleats may act as a channel resulting in excessive diaper leakage and the pleats in the crotch area make the infant's bottom uncomfortable when sitting especially while the diaper is not saturated.

SUMMARY OF THE INVENTION

The present invention overcomes the disadvantages of both of the prior art diapers. The elastic members are placed according to the present invention less than $\frac{3}{4}$ inch from the absorbent pad thereby reducing the width of the crotch seals rendering the diaper more comfortable. However, the elasticized strips are so positioned that the tension thereon can be maintained and adjusted so that no transverse pleats are formed in the diaper, thereby eliminating excessive leakage and discomfort tof the pleats' prior saturation. This is accomplished by extending the elasticized members the entire length of the pad and over the ears of the contoured pad.

The concept of the invention features a disposable diaper which is contoured in an hour-glass configuration and has an absorbent body between a top sheet and a backing sheet with elastic members secured to the backing sheet and extending the full length of the absorbent pad, but less than $\frac{3}{4}$ inch from the absorbent body in the crotch area. The tension on the elastic members is such that there will be pleats only along the crotch seals and substantially no pleats transversely along the crotch area of the diaper. The elasticized members extend the full length of the absorbent pad assembly.

DETAILED DESCIPTION OF THE INVENTION

Figure 1:
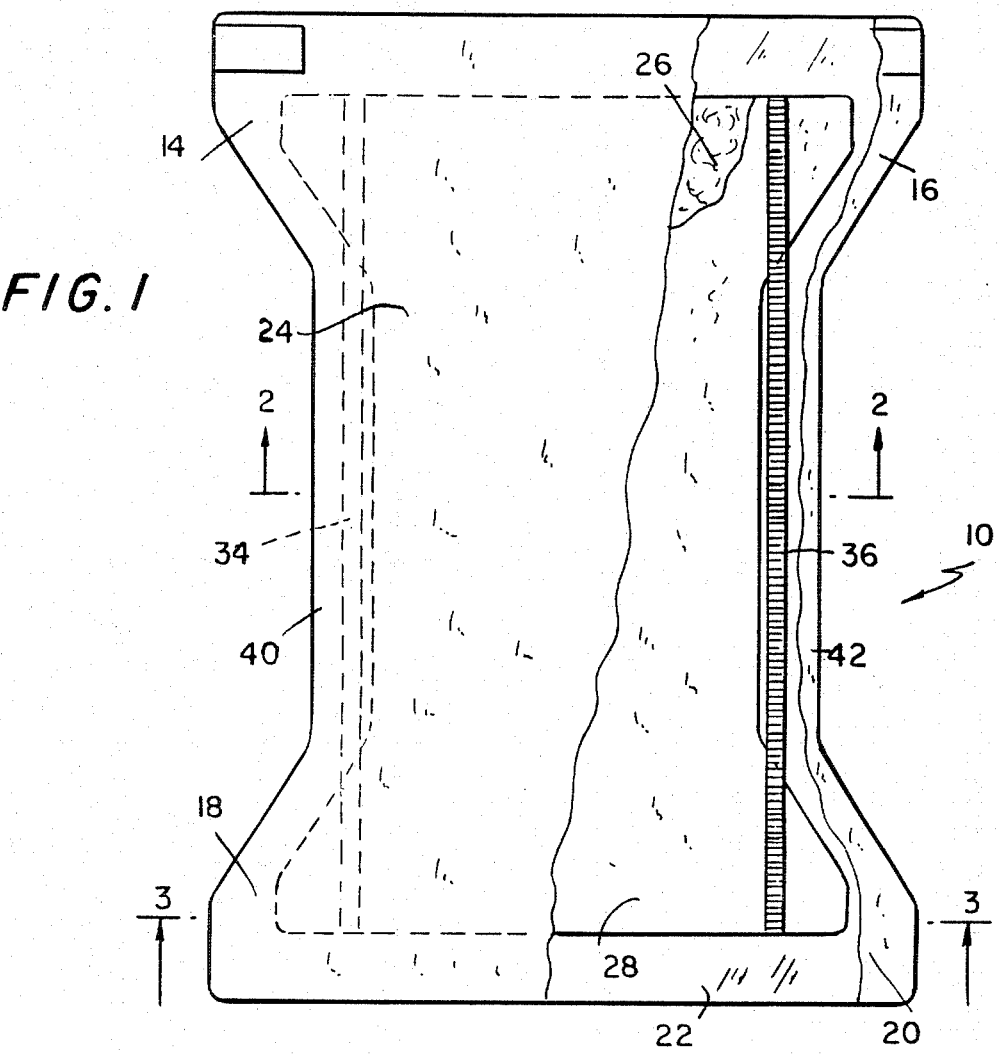
FIG. 1 is a plan view of a diaper constructed in accordance with the concepts of the present invention.
Figure 2:
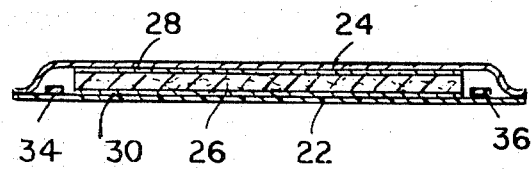
FIG. 2 is a transverse sectional view taken along the plane of line 2—2 in FIG. 1 through the crotch portion of the diaper; and, FIG. 3 is a transverse view taken along the plane of line 3—3 in FIG. 1.

With continuing reference to the accompanying drawing, wherein like reference numerals designate similar parts throughout the various views, reference numeral 10 generally designates an elasticized and contoured disposable diaper constructed in accordance with the concepts of the present invention. The diaper is of an hour-glass configuration having a crotch area 12 and four portions of greater width defining ears 14, 16, 18 and 20. The diaper includes a backing sheet 22 of an impervious material, such as polyethylene or polypropylene film. A top sheet 24, preferably of a typical nonwoven bonded (e.g. by resin latex) rayon or rayon-polyester fiber sheet or a spun-bonded sheet of polyethylene or polypropylene fibers, is sealed preferably by hot melt lines to the backing sheet along the peripheral edges of the diaper. An absorbent pad 26 is disposed between the top sheet 24 and the backing sheet 22 and may be of conventional wood fluff (e.g. from chemical, semi-chemical or theremo-mechanical pulp) or the like. An upper wadding sheet 28 and a lower wadding sheet 30 are provided, the pad and the wadding sheet conforming generally in contour to the hour-glass shape forming ears within the confines of ears 14, 16, 18 and 20. The absorbent pad 20 and wadding sheets 28 and 30 form an absorbent pad assembly which have ears within the confines of ears 14, 16, 18 and 20.

Figure 3:
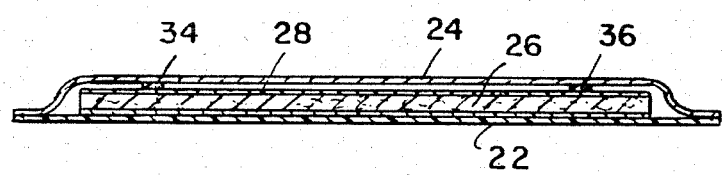

A pair of elasticized strips 34 and 36, which may be provided with adhesive on at least the bottom surface thereof and optionally on the top surface or applied separately in these locations thereof, are bonded with the adhesive to the backing sheet 22 in the crotch area immediately adjacent the pad 26 and in all events less than $\frac{3}{4}$ inch from the pad. The adhesive may be used as a continuous layer or discrete spots or lines, and it may be any conventional hot melt or pressure-sensitive adhesive and, preferably, one that, at ambient temperatures is flexible and extensible (i.e. elastic-like) in nature. The strips 34 and 36 extend the full length of the absorbent pad assembly and overlie the earred portion of the upper wadding sheet 28, as shown in FIG. 3, so that the tension on the heat sealed backing sheet and top sheet provided by the elasticized strips is such that the pleats are only formed in the crotch seals formed by the elasticized strips and portions 40 and 42 outwardly thereof and between the elasticized strips and the pad, while no significant number of pleats are formed in the crotch area 12. The top and bottom wadding sheets may be the conventional paper or tissue heretofore used in the art (i.e. cellulosic fibers) or may be formed of hydrophobic fibers (e.g. polyester, polyethylene or polypropylene) or rendered hydrophobic by suitable and conventional treatments (e.g. by resins).

The elastic strips 34 and 36 may be varied in widths but generally from about 3–5 mm on the lower end to 10–12 mm on the upper end with a range of about 5 to 8 mm being preferred. The adhesive width may be somewhat greater or lesser than that of the elastic strips and typically for a 6 mm elastic strip would range from about 4–12 mm. Typical thicknesses of strips 34 and 36 range from a few mils (e.g. 1 to 5) to 15 or 20 mm, with the higher ranges more general for foams.

One conventional process for making the diapers of this invention employs a conventional fluff forming technique using, preferably, wadding sheets to carry the fluff pad between them. This composite is suitably cut to shape and then laid down on the larger size backsheet 22. Before applying the elastic strips 34 and 36, the diaper, while going through the fabricating machine, is matained by suitable means (e.g. clamping fingers) in its fully extended position and the elastic strips are applied and secured to the diaper backsheet at an elongation of about 40 to 80% beyond its relaxed length and preferably at about 50 to 70% elongation and more preferably at about 55 to 65% elongation (e.g. typically 60% elongation). The top sheet 24 is then applied and secured as by adhesive means to the backsheet around the peripheral edges (outwardly of the pad 26) and to the ears of the absorbent pad assembly. As described above, the top sheet 24 may be, and preferably is, secured to the elastic strips 34 and 36 as well. Reference is also hereby made to U.S. Pat. Nos. 4,022,456 and 4,081,301 for further specific details as to apparatus and methods for assembling elastic absorbent structures as generally herein contemplated and such patents are hereby incorporated by reference thereto. Since it is preferred that the ends of the elastic strips, where they overlie (or underlie) the ears of the absorbent pad assembly, the strips are bonded to the absorbent pad assembly along the full length of the ears. By the foregoing construction, upon contraction of the elastic strips, only the back sheet and other elements secured to the elastic strips are contracted to form pleats and the overall diaper generally assemes a bowl-like shape which facilitates placing the diaper on the baby and permits a better fit as well. The bonding of the strips to the ears of the absorbent pad assembly controls and reduces the formation of transverse pleats in the pad assembly. This is because the elastic members are bonded, not only to the backing sheet, but to the ears of the absorbent pad assembly and the absorbent pad assembly functions to stiffen against tension.

The elastic strips 34 and 36 may be of any suitable construction and materials such as the conventional rubberized (or otherwise elastomerized) fibers or may be simply a strip of elastomeric resin or foamed resin which may or may not be provided with adhesive. Such strips are generally available as double sided transfer tapes (e.g. 3M Co. St. Paul, Minn. tape No. 465 high tack pressure-sensitive tape).

What is claimed is:

1. A disposable diaper comprising a backing sheet, an absorbent pad assembly on said backing sheet, a top sheet overlying said absorbent pad assembly, said top sheet being secured to said backing sheet on at least two opposite peripheral edges thereof, opposed elastic members secured to said backing sheet outwardly of said absorbent pad in the central portions of said two opposite peripheral edges to define crotch seals along the side edges of said diaper, said absorbent pad assembly being of an hour-glass shape defining ears spaced from said crotch area, said elastic members extending the entire length of said ears, said absorbent pad assembly including an absorbent pad and an upper tissue wadding sheet overlying said absorbent pad, said elastic members being bonded to said backing sheet spaced outwardly of said absorbent pad assembly and along said crotch area and being spaced from said crotch area less than ¾ inch from said absorbent pad assembly, said elastic members being bonded to said tissue wadding sheet along the entire length of said ears so that the minimum resistance of said tissue wadding sheet relative to said absorbent pad will result in the tension on said elastic members forming only pleats in said crotch area and no transverse creases or pleats in said absorbent pad in said crotch area.

* * * * *